United States Patent [19]
Couderc et al.

[11] Patent Number: 5,926,271
[45] Date of Patent: Jul. 20, 1999

[54] LASER-INDUCED FLUORESCENCE DETECTOR HAVING A CAPILLARY DETECTION CELL AND METHOD FOR IDENTIFYING TRACE COMPOUNDS IMPLEMENTED BY THE SAME DEVICE

[75] Inventors: Francois Couderc, Toulouse; Michel Nertz, Sainte Foy D'Aigrefeuille; Georges Nouadje, Toulouse, all of France

[73] Assignee: Zeta Technology, Ramonville Saint-Agne, France

[21] Appl. No.: 08/982,256

[22] Filed: Dec. 1, 1997

Related U.S. Application Data

[63] Continuation-in-part of application No. 08/575,479, Dec. 20, 1995, abandoned.

[51] Int. Cl.$^6$ ......................................................... G01J 3/30
[52] U.S. Cl. .......................................... 356/318; 356/319
[58] Field of Search ...................................... 356/318, 319

[56] References Cited

U.S. PATENT DOCUMENTS

| | | | |
|---|---|---|---|
| 4,348,107 | 9/1982 | Leif | 356/317 X |
| 4,548,498 | 10/1985 | Folestad et al. | 356/318 |
| 4,714,345 | 12/1987 | Schrader | 356/301 X |
| 5,037,199 | 8/1991 | Hlousek | 356/246 |
| 5,061,361 | 10/1991 | Gordon | 250/576 X |

*Primary Examiner*—Robert Kim
*Attorney, Agent, or Firm*—Young & Thompson

[57] ABSTRACT

A laser-induced fluorescence detector comprises a laser beam emitting device, a dichroic mirror to deviate the laser light orthogonally, a lens with a small numerical aperture, a ball lens, a unique cell within a capillary, the cell receiving a solute containing at least one unknown fluorescent substance at the laser wavelength, the same device collecting the fluorescence emitted by the fluorescent substance, with optical filters, a photomultiplier tube, and a computer for displaying results of the analysis. The ball lens converts the laser beam into a very small divergent beam, which allows a high irradiated volume in the capillary cell. The cell employs controlled geometric contours to prevent laminar mixing and turbulence during liquid flow, and the collecting device is a high numerical aperture device, for example, a ball lens.

9 Claims, 2 Drawing Sheets

LASER-INDUCED FLUORESCENCE DETECTOR HAVING A CAPILLARY DETECTION CELL AND METHOD FOR IDENTIFYING TRACE COMPOUNDS IMPLEMENTED BY THE SAME DEVICE

This is a continuation-in-part application of U.S. Ser. No. 08/575,479 which was filed on Dec. 20, 1995, now abandoned.

TECHNICAL FIELD

The present invention relates to a laser-induced fluorescence detector. The invention also relates to a method for identifying unknown substances implemented by this device.

BACKGROUND OF THE INVENTION

This invention is particularly concerned with the identification of unknown substances and the recognition of trace compounds which are separated by different means:
 a) by HPLC (High Performance Liquid Chromatography) and detected post column on small bore activated or inactivated capillaries at the outlet of the column,
 b) by micro-HPLC (High Performance Liquid Chromatography) and detected on column in a narrow bore capillary,
 c) by CE (Capillary Electrophoresis) or CEC (Capillary Electro Chromatography) and detected on column.

Previous techniques, which include Laser-Induced Fluorescence (LIF) detection with HPLC and CE techniques, together with narrow bore silica capillary have been successfully employed to assay samples whose molecular structure is relatively small.

HPLC and CE techniques, associated with UV-absorption detectors are widely used for the identification of a wide range of compounds in unknown substances. Nevertheless, UV-absorption detectors are limited in terms of sensitivity. To identify very low concentrations of substances, the LIF detection is therefore necessary.

Laser fluorimetry is very different from arc lamp fluorimetry and has some main characteristics, which are advantageous with a small volume detector. The produced fluorescent radiation is directly proportional to the intense laser excitation light. The amplitude stability of the laser also helps to minimize background noise level.

With LIF detections at least four problems have to be solved:
 maximizing the irradiated volume,
 maximizing the collection efficiency,
 maintaining the best separation efficiency (variance due to the detection), and
 maintaining the lowest laser light scattering.

The fluorescence dF emanating from a volume dV is given by:

$$dF = c \; \epsilon \; \phi(P/S) \; dV$$

where
 c is the fluorophor concentration
 $\epsilon$ is the molar absorption factor of the fluorophor
 $\phi$ is the fluorescence quantum efficiency of the fluorophor.
 P is the power of the light exciting the molecules in the internal diameter of the capillary.
 S is the section of the light beam exciting the molecules To get the highest fluorescence level, the excited volume containing the fluorescent molecules must be as large as possible.

Gordon [U.S. Pat. No. 5,061,361] discloses a method and apparatus for increasing UV-absorption detector sensitivity in a Capillary Zone Electrophoresis detector. The detection means comprise a unique cell on the capillary presenting a dilated zone in the detection area, that employs controlled geometric contours to prevent laminar mixing and turbulence when using electro-osmotic pumping or pressure pumping. This so-called "enlarged capillary cell (or ovoid cell)" in which an unknown substance is migrating is subjected to an ultraviolet light. Part of the light is absorbed by the unknown substance.

Schrader [U.S. Pat. No. 4,714,345] specifies (column 1 line 15–20) that "The theorical discussions (for Raman spectrometry) show that the LASER radiation has to be focused and the liquid sample has to be arranged at the focus."

Hlousek [U.S. Pat. No. 5,037,199] discloses a cell assembly for use in spectrophotometric analysis or detection on column of a substance within a small sample volume. A first ball lens can be used for transmitting a non coherent light beam which excites a sample, while another ball lens is used for collecting the fluorescence. The exciting beam is arranged to be focused inside the capillary, and an index matching fluid may be used to facilitate the light transmission in the capillary bore.

Buttner and Beck [EP 0 634 651 A1] propose a variant of an enlarged capillary for a CE system with UV-absorption detector or conventional fluorimeter, in which the fluorescence induced by a non coherent light is collected orthogonally, and the excitation beam is focused in the enlarged end part of the capillary.

The mode of focusing used in the example cited above is not compatible with a large illuminated volume required for laser-induced fluorescence.

Hernandez [1] [2] teaches that a high numerical aperture is required to collect the highest level of fluorescence on a capillary and to have the lowest background noise, and shows the evolution of the fluorescence versus the internal diameter of the capillary for a high numerical aperture objective. The intensity of fluorescence features a high increase for very low diameters (<15 $\mu$m), then stays nearly constant, and then decreases for higher diameters.

The use of a cell with controlled geometric contours prevents laminar mixing and turbulence which are necessary to maintain the best separation efficiency.

The main causes of light scattering in laser-induced fluorescence are:
 reflections on the optical elements, including the silica capillary walls,
 scattering due to the buffers flowing in the capillary,
 physical phenomena such as Raman scattering.

In a collinear arrangement, these disadvantages may be overcome, since Raman back-scattering is avoided in the excitation axis [1] (compared to its nearly maximum level in a direction orthogonal to the incident light). The other causes may be mastered by adjusting properly the light paths and placing at appropriate location in the fluorescence light path spatial filter or diaphragm of selected diameter (0.5 to 1.5 mm).

The objective of this invention is to propose a laser-induced fluorescence detector device, for HPLC or Capillary Electrophoresis, with an increased sensitivity while employing capillaries having an enlarged capillary detection cell with an internal diameter substantially greater than 15 $\mu$m and a sapphire ball lens, allowing the highest irradiated volume and the best fluorescence collection efficiency.

SUMMARY OF THE INVENTION

This objective is reached with a laser-induced fluorescence detector comprising:

means for emitting a laser beam, means for optimizing the volume irradiated by the laser beam, a unique cell within a capillary, the cell receiving a solute containing at least one unknown fluorescent substance at the laser wavelength, means for collecting the fluorescence emitted by the fluorescent substance, means for filtering the collected fluorescence, photomultiplier tube means for processing the filtered and collected fluorescence, and means for analyzing signals generated by the photomultiplier tube means and for displaying results of the analysis, wherein the cell employs controlled geometric contours to prevent laminar mixing and turbulence during liquid flow, and collecting means include high numerical aperture means.

Enlarged capillary with controlled geometric contours for the cell allow a higher amount of unknown substance to be excited by the laser beam than in a classical cylindrical capillary. The use of high numerical aperture means for fluorescent beam collecting results in a maximization of the collection efficiency and maintains the lowest laser light scattering. The characteristics of the laser beam gives a unique opportunity to master the maximum irradiance into the capillary.

The sensitivity of a laser-induced fluorescence detector is significantly improved by using the type of cell disclosed in Gordon, provided that the whole volume of the cell is irradiated by the laser beam. Our optical system is designed to focus the laser beam inside the ball lens to get a diverging beam on the cell. By adjusting the elements of the system, the output beam diameter can be modified so that the total internal volume of the cell is illuminated. The use of controlled geometric contours to prevent laminar mixing and turbulence is required to maintain the best separation efficiency.

In a first preferred embodiment, the cell, which is fabricated into a fused silica capillary, is substantially egg-shaped. In a second embodiment, the cell has an elliptic shape. In both embodiments, the emitting means and the collecting means are disposed collinearly with one sapphire ball lens. In a third embodiment, emitting and collecting means can be disposed orthogonally with two truncated sapphire ball lenses for orthogonal detection.

The use of a conventional cell on a low internal-diameter capillary (which allows very high electrophoretic or chromatographic resolutions) results in a low sensitivity. Combining an ovoid cell within a small internal-diameter capillary and a high numerical aperture ball lens allowing a controlled divergence of the laser beam results in an optimized illuminated volume and the best fluorescence collection yield, and thus in a higher sensitivity. Thus, a low internal diameter for the capillary is no more antinomic with a high detection sensitivity. Moreover the collinear arrangement, as used in a preferred embodiment, provides a lower light scattering, resulting in a higher signal to noise ratio, hence in a higher sensitivity, compared to other optical arrangements.

A sapphire ball lens, combining high refractive index and spherical shape, is used to obtain a high numerical aperture, which can be increased by using an index matching liquid between the ball lens and the capillary. Moreover, the good light transmission range of the sapphire allows the possible future use of LIF detection in the UV and IR domains, with appropriate lasers, at a reasonable cost.

Laser-induced fluorescence detectors according to the invention can be implemented in Liquid Chromatography or Capillary Electrophoresis systems.

Another aspect of the invention relates to a method for identifying unknown substances, comprising the following steps:

emitting a laser beam towards a capillary including a cell through which a solute flows containing at least one unknown fluorescent substance at the laser wavelength, collecting the fluorescence emitted by the fluorescent substance, filtering the collected fluorescence, transmitting the filtered and collected fluorescence to photomultiplier tube means, and analyzing signals generated by the photomultiplier tube means and displaying results of the analysis, wherein the emitting step and the collecting step are achieved collinearly. The emitting step includes a step for concentrating the laser beam in a ball lens and directing the resulting diverging beam into the ovoid cell. The collecting step includes the same ball lens, which has a very high numerical aperture. The ovoid cell has controlled geometric contours to prevent laminar mixing and turbulence during solute flow.

By implementing the method according to the invention, an increase of sensitivity by ten leaves several options to an instrument developer. For example, a low power laser can be used for the same sensitivity, but with a significant price reduction which may be well above 70%, because it allows the possible use of a laser diode or diode based lasers (lasers pumped by diode, frequency doubled or tripled laser diodes). This price reduction is an important factor for an increase of the number of potential users of these identification techniques. Moreover it makes possible to detect very low concentration species eluted in a capillary, which cannot be detected with other classical laser-induced fluorescence means.

BRIEF DESCRIPTION OF THE DRAWINGS

The invention is illustrated, by way of example, in the accompanying drawings, in which.

DETAILED DESCRIPTION OF PREFERRED EMBODIMENT

Figure 1A:
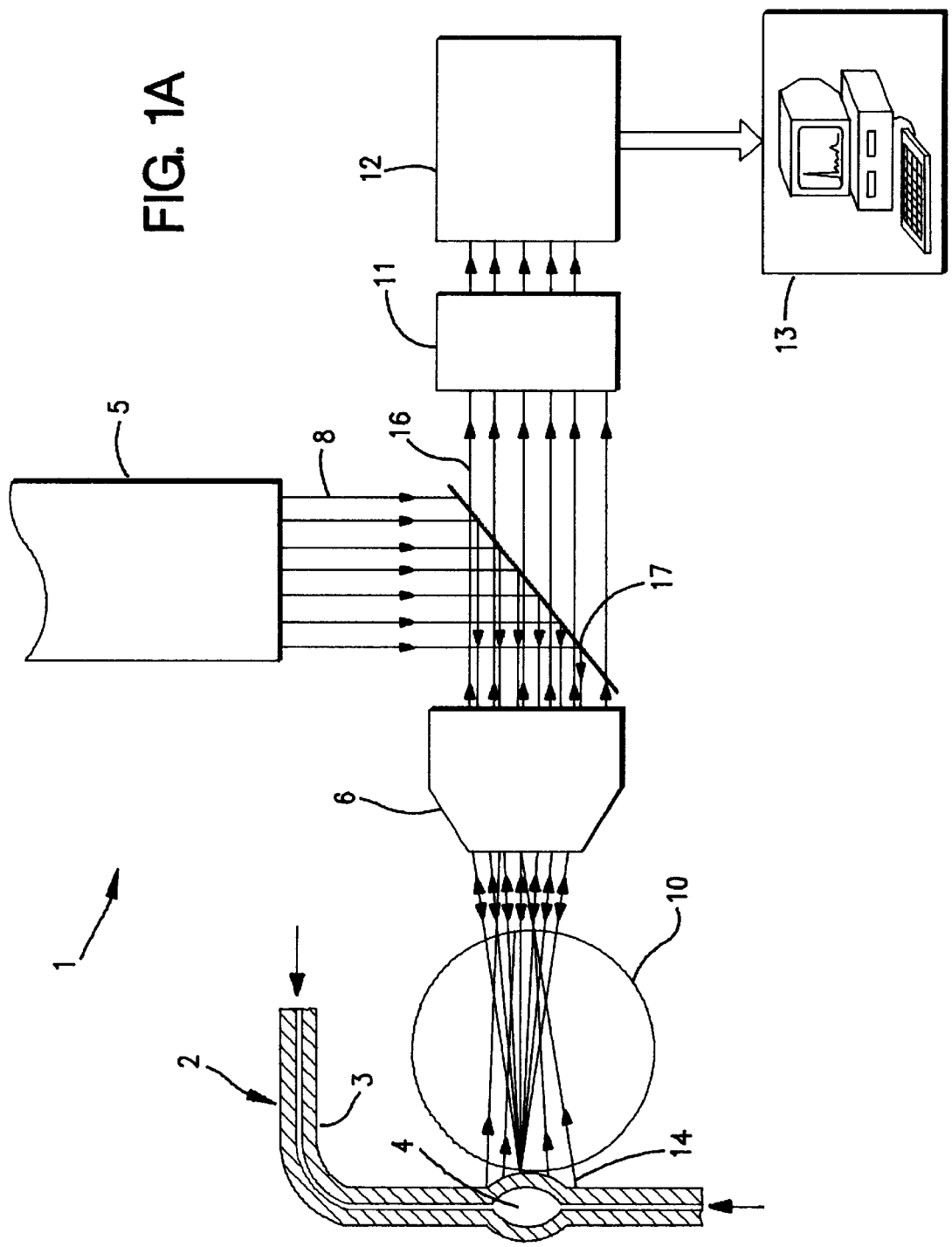
FIG. 1A shows a schematic view of a first embodiment a detector according to the invention, with a Collinear optical arrangement.

In a first embodiment (FIG. 1A), where emitting and collecting means are disposed colinearly, a detector 1 comprises a laser source 5 emitting a laser beam 8, a dichroic mirror 17 deviating orthogonally the laser beam 8 through a small numerical aperture lens 6 towards a small diameter (1–3 mm) sapphire ball lens 10 operating as a high numerical aperture means for illuminating with the laser beam 8 an ovoid cell 4 and for collecting induced fluorescence and providing a substantially parallel collected beam 16. The collected beam 16 is filtered through a set of filters 11 and applied to a photomultiplier tube 12 delivering signals indicative of the fluorescence intensity. The signals are processed and analyzed by a computer 13 or the like. The ball lens converts the slightly converging beam coming from lens 6 into a small divergent beam, which matches the total internal volume of the ovoid cell, when the converging beam characteristics are optimized (laser beam diameter, numerical aperture of lens 6, distance between lens 6 and ball lens 10. To obtain this small diverging beam, the laser beam reaches the lens 6 slightly off-axis, then reaches the ball lens 10 with a small angle and off-axis. By adjusting the distance between the lens 6 and the ball lens 10, the laser beam can be focused inside the ball lens, the focus point being close to the external surface of the ball lens, so that the diverging beam coming from the ball lens onto the ovoid cell may be adjusted from 20 to 250 μm.

The high numerical aperture sapphire ball lens converts the rapidly diverging cone of fluorescent light emanating from the sample volume to a slowly diverging cone of light that is virtually collimated by the lens 6 and can be coupled to suitable light sensing means such as the photomultiplier tube 12.

Moreover, the collinear arrangement using the same optical device for emitting and collecting light avoids the difficulty to put two optical devices at the same location close to a small diameter capillary (commonly 375 μm outside diameter), as it is necessary in an orthogonal arrangement.

Figure 1B:
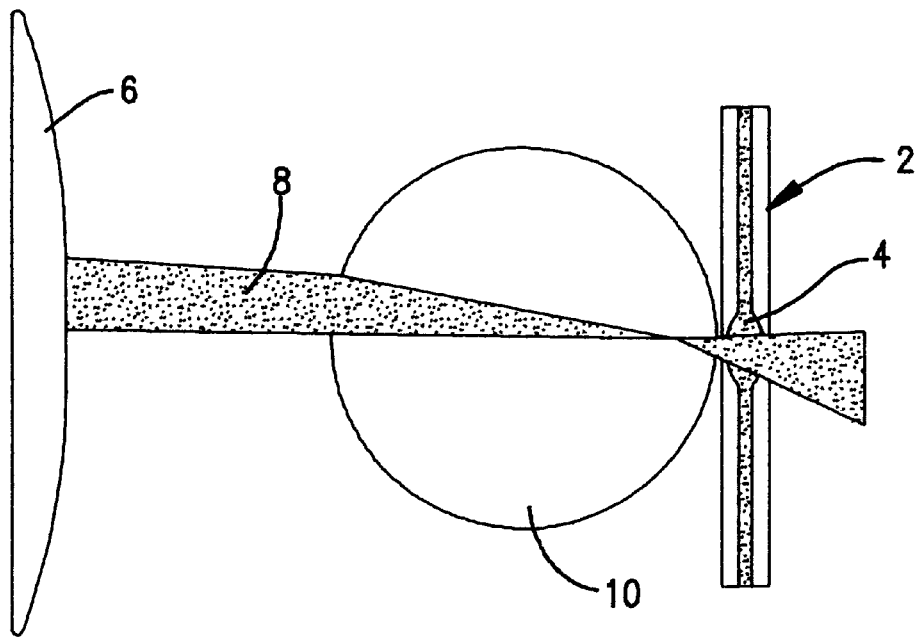
FIG. 1B shows details of the laser beam profile through the ball lens and ovoid cell combination.
Figure 1B:
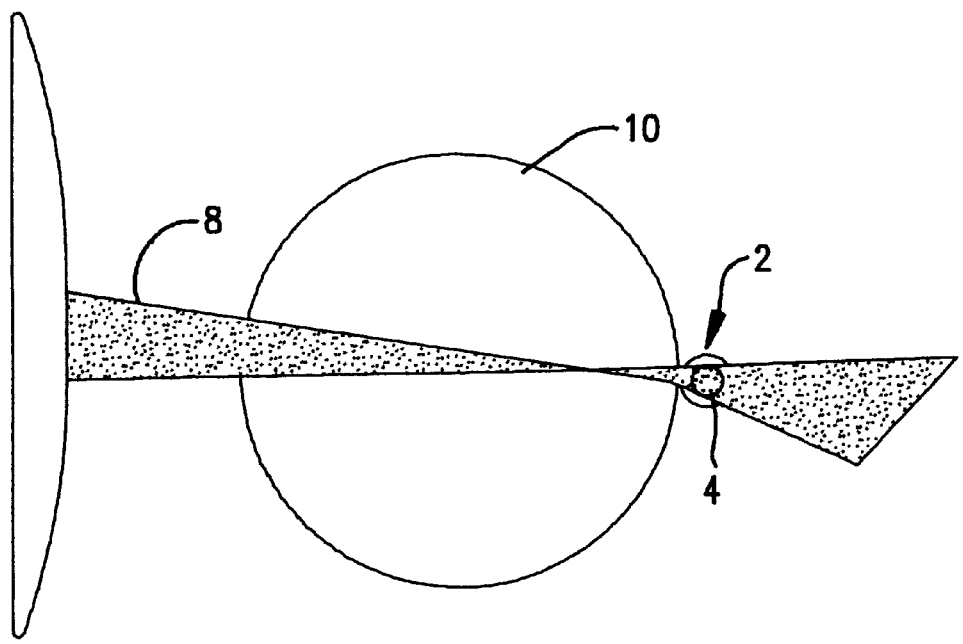

FIG. 1B shows the high numerical aperture ball lens with the slightly convergent beam focused in the ball lens, resulting in a diverging laser beam emerging from the ball lens and illuminating the total internal volume of the ovoid cell.

A liquid 3 containing an unknown substance which fluoresces at the laser wavelength, flows into the cell 4 from a chromatography column (or microcolumn) or from a capillary electrophoresis system (non represented).

In the case of a chromatography column (or microcolumn), the capillary 2 is a small bore activated or deactivated capillary with an internal diameter from 50 to 350 μm depending on the flow rate, since in the case of an electrophoresis system, the capillary 2 is a narrow bore capillary with an internal diameter below 100 μm.

Equipment

In a preferred embodiment of a detector 1 according to the invention, the laser source 5 can be a 488 nm Argon ion laser from ILT, Salt Lake City (Utah), with a maximum emission power of 7 mW, or a 543 nm HeNe laser from Melles Griot, Irvine (Calif.), with a maximum emission power of 1,5 mW. The lens 6 is a 5×0,12 Achrostigmat from Zeiss (Germany).

The capillary 2 is 70 cm Fused silica capillary (ref. 75 μm I.D.×375 μm O.D), from Polymicrotechnology Phoenix (Ariz.). The capillary 2 is included in a electrophoresis device, for example a SpectraPHORESIS 100 TSP, from Fremont (Calif.) The photo-multiplier-tube (PMT) 12 is a referenced R928 PMT from Hamamatsu Photonics (Japan). Output signals from the PMT are processed by a computer 13, for example a 486 Personal Computer, using a data acquisition and processing 10 software.

REFERENCES

[1] L. Hernandez , J. Escalona, and N. Joshi, J. Chromatogr. 559 (1991) 183–196;
[2] L. Hernandez, N. Joshi, E. Murzi, F. Verdeguer, J. C. Mifsud, and N. Guzmaan, J. Chromatogr. 652 (1993) 399–405;

PATENTS

U.S. Pat. Nos.:

5,037,199 Hlousek
4,348,107 Leif
4,714,345 Schrader
4,548,498 Folestad
4,675,300 Zare
5,061,361 Gordon
EP 0 634 651 A1 BUTTNER & BECK Date of publication Jan. 18, 1995

We claim:

1. A laser-induced fluorescence detector comprising:

a laser source for emitting a laser beam, a unique cell substantially egg-shaped within a capillary, said cell receiving a solute containing at least one unknown fluorescent substance at the laser wavelength and employing controlled geometric contours to prevent laminar mixing and turbulence during liquid flow, means for illuminating by said laser beam said fluorescent substance flowing in the capillary, said illuminating means including a ball lens for converting a slightly converging laser beam coming from a small numerical aperture lens into a small divergent beam illuminating the volume of the cell, means for collecting the fluorescence emitted by the fluorescent substance, said collecting means including high numerical aperture means; said small numerical aperture lens, said capillary and said collecting means being disposed collinearly, and said ball lens being further used as the high numerical aperture means, means for filtering said collected fluorescence, photomultiplier tube means provided for processing said filtered and collected fluorescence, and means for analyzing signals generated by said photomultiplier tube means and for displaying results of said analysis, wherein said illuminating means and said cell are structured and arranged so as to maximize the volume irradiated by said laser beam.

2. A laser-induced fluorescence detector according to claim 1, wherein the means for emitting the laser beam, the small numerical aperture lens, the ball lens and the cell are arranged in such a way that the laser beam reaches the small numerical aperture lens slightly off-axis and then reaches the ball lens with a small angle and off-axis.

3. A laser-induced fluorescence detector according to claim 2, wherein the distance between the small numerical aperture lens and the ball lens is adjusted so as to focus the laser beam inside the ball lens, the focus point being close to the external surface of the ball lens.

4. A laser-induced fluorescence detector according to claim 3, wherein a liquid is between the capillary and the ball lens.

5. A laser-induced fluorescence detector according to claim 1, wherein the cell is substantially elliptic.

6. A laser-induced fluorescence detector according to claim 1, wherein the cell is fabricated into a fused silica capillary.

7. A Capillary Electrophoresis apparatus including a laser-induced fluorescence detector according to claim 1.

8. A Liquid chromatography apparatus including a laser-induced fluorescence detector according to claim 1.

9. A method for identifying unknown substances, comprising the following steps:

emitting a laser beam towards a unique cell substantially egg-shaped within a capillary, said cell receiving a solute containing at least one unknown fluorescent substance at the laser wavelength and employing controlled geometric contours to prevent laminar mixing and turbulence during liquid flow, illuminating said fluorescent substance flowing in the capillary, by said laser beam with a high numerical aperture ball lens which converts a slightly converging laser beam coming from a small numerical aperture lens into a small divergent beam illuminating the volume of the cell, collecting the fluorescence emitted by the fluorescent substance in the ball lens, filtering said collected fluorescence, transmitting the filtered and collected fluorescence to a photomultiplier tube, analyzing signals generated by the photomultiplier, and displaying results of the analysis, wherein the volume illuminated by said laser beam is maximized.

* * * * *